United States Patent [19]

Meyer et al.

[11] 3,974,290
[45] Aug. 10, 1976

[54] VASODILATING AND ANTIHYPERTENSIVE COMPOSITIONS AND METHODS OF EFFECTING VASOLIDATION AND TREATING HYPERTENSION UTILIZING 2-AMINO-4H PYRANE AS THE ACTIVE AGENT

[75] Inventors: Horst Meyer; Friedrich Bossert, both of Wuppertal; Wulf Vater, Opladen; Kurt Stoepel, Wuppertal, all of Germany

[73] Assignee: Bayer Aktiengesellschaft, Germany

[22] Filed: Nov. 25, 1974

[21] Appl. No.: 526,846

Related U.S. Application Data

[62] Division of Ser. No. 375,809, July 2, 1973, Pat. No. 3,897,462.

[30] Foreign Application Priority Data

July 19, 1972 Germany............................. 2235406

[52] U.S. Cl............................................. 424/283
[51] Int. Cl.².......................................... A61K 31/35
[58] Field of Search.................................. 424/283

[56] References Cited
UNITED STATES PATENTS 3,707,482  12/1972  Laliberte............................ 424/283

OTHER PUBLICATIONS

B380,446, Jan. 1975, Bender et al., 424/283.

*Primary Examiner*—Sam Rosen

[57] ABSTRACT

2-Amino-4 H-pyrane derivatives of the formula

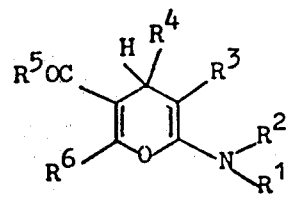

wherein
$R^1$ and $R^2$ are the same of different and each is hydrogen or straight- or branched-chain alkyl;
$R^3$ is straight- or branched-chain alkyl, phenyl or —COOR' wherein R' is a straight, branched or cyclic saturated or unsaturated aliphatic hydrocarbon;
$R^4$ is straight, branched or cyclic alkyl or alkenyl, aryl unsubstituted or substituted by 1, 2 or 3 of the same or different substituents selected from the group consisting of akyl, alkoxy, halogen, nitro, cyao, trifluoromethyl, carbalkoxy, and —SO$_n$ alkyl wherein $n$ is 0, 1 or 2, or
$R^4$ is naphthyl, quinolyl, pyridyl, thienyl or furyl unsubstituted or substituted by alkyl, alkoxy or halogen;
$R^5$ is straight, branched or cyclic alkyl or —OR'' wherein R'' is a straight, branched or cyclic hydrocarbon or said hydrocarbon interrupted by 1 or 2 oxygen atoms; and
$R^6$ is hydrogen or alkyl;

are useful for their strong coronary action and as antihypertensive agents.

64 Claims, No Drawings

VASODILATING AND ANTIHYPERTENSIVE COMPOSITIONS AND METHODS OF EFFECTING VASODILATION AND TREATING HYPERTENSION UTILIZING 2-AMINO-4H PYRANE AS THE ACTIVE AGENT

This is a division of parent application Ser. No. 375,809, filed July 2, 1973 now U.S. Pat. No. 3,897,462, issued on July 29, 1975.

The present invention relates to 2-amino-4 H-pyrane derivates, to processes for their production, to pharmaceutical compositions embodying said compounds as the active ingredient and to their use as vasodilators and antihypertensive agents.

It has already been disclosed that the reaction of α,β-unsaturated carbonyl compounds with enamines leads to 2,3-dihydro-4 H-pyranes, for example:

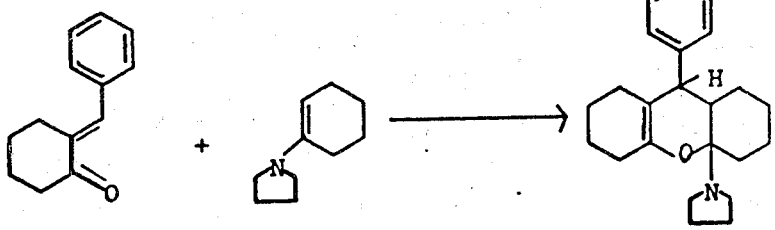

(compare I. W. Lewis, P. L. Myers, M. I. Readhead, J. Chem. Soc. C, 1970, 771).

Inamines react similarly (J. Ficini, A. Krief, Tetrahedron Letters 1969, 1427).

Hitherto, nothing has been disclosed regarding a possible circulation-influencing effect of these 4 H-pyranes.

It has furthermore been disclosed that the reaction of 4-nitrobenzylidene-acetylactone with potassium cyanide in an alkaline medium yields 3-acetyl-5-amino-2-methyl-4-(p-nitrophenyl) furane (see equation):

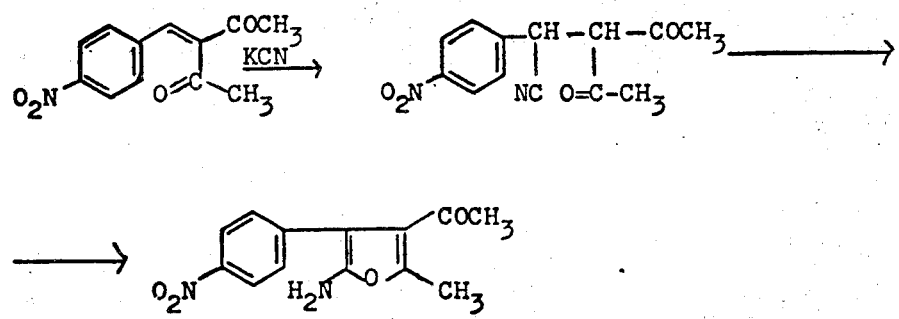

(compare I. P. Sword, J. Chem. Soc. C, 1970, 1916).

More particularly, the present invention is concerned with 2-amino-4 H-pyrane derivatives of the formula:

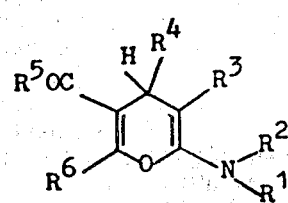   I wherein
R¹ and R² are the same or different and are each hydrogen or straight- or branched-chain alkyl, especially lower alkyl;

R³ is straight- or branched-chain alkyl, especially lower alkyl, phenyl or —COOR' wherein R' is a straight, branched or cyclic saturated or unsaturated aliphatic hydrocarbon, especially lower alkyl, lower alkenyl, lower alkynyl, cycloalkyl of 3 to 7 carbon atoms or cycloalkenyl of 3 to 7 carbon atoms;

R⁴ is straight, branched or cyclic alkyl or alkenyl, especially lower alkyl, lower alkenyl, cycloalkyl of 3 to 7 carbon atoms or cycloalkenyl of 3 to 7 carbon atoms, aryl, especially phenyl, unsubstituted or substituted by 1, 2 or 3 of the same or different substituents selected from the group consisting of alkyl, especially lower alkyl, alkoxy, especially lower alkoxy, halogen, nitro, cyano, trifluoromethyl, carbalkoxy, especially carb(lower alkoxy), and —SO$_n$ alkyl, especially lower alkyl, wherein $n$ is 0, 1 or 2, or R⁴ is naphthyl, quinolyl, pyridyl, thenyl or furyl unsubstituted or substituted by alkyl, especially lower alkyl, alkoxy, especially lower alkoxy, or halogen;

R⁵ is straight, branched or cyclic alkyl, especially straight- or branched-chain lower alkyl, or cycloalkyl of 3 to 7 carbon atoms, or —OR'' wherein R'' is a straight, branched or cyclic hydrocarbon, or said hydrocarbons interrupted by 1 or 2 oxygen atoms, especially straight- or branched-chain lower alkyl, lower alkenyl, lower alkynyl, cycloalkyl of 3 to 7 carbon atoms, cycloalkenyl of 3 to 7 carbon atoms, or said lower alkyl, lower alkenyl, lower alkynyl, cycloalkyl of 3 to 7 carbon atoms, or cycloalkenyl of 3 to 7 carbon atoms interrupted by 1 or 2 oxygen atoms; and R⁶ is hydrogen or alkyl, especially lower alkyl.

The 2-amino-4 H-pyrane derivatives of the present invention are particularly useful because they exhibit a strong coronary action, particularly a vasodilating action, as well as a good antihypertensive effect. The compounds of the present invention may be produced by reacting an α,β-unsaturated dicarbonyl compound of the formula

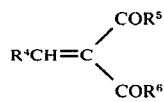    II wherein $R^4$, $R^5$ and $R^6$ are as above defined,
a. with an inamine of the formula The compounds according to the invention, of the general formula I, are distinguished by a long-lasting strong vasodilating action. Hitherto, no pharmaceutical action of such 2-amino-4 H-pyrane derivatives has been disclosed. The compounds according to the invention represent new agents for the treatment of circulatory illnesses and are hence an enrichment of pharmacy.

If 2'-trifluoromethylbenzylideneacetoacetic acid ethyl ester and 1-N,N-diethylaminopropine are used as starting compounds, the course of the reaction can be represented by the following equation:
Process Variant (a):

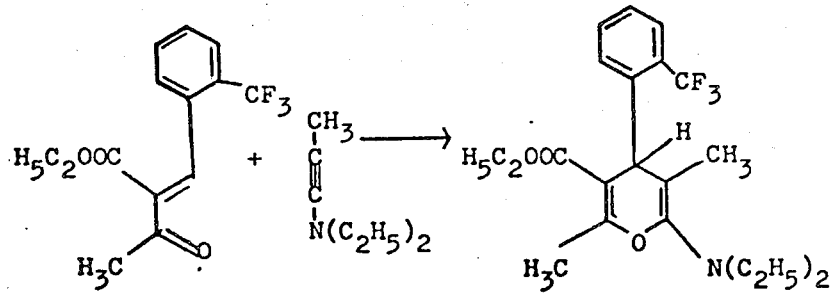

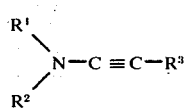    III

If 3'-nitrobenzylideneacetoacetic acid methyl ester and cyanoacetic acid ethyl ester are used as starting compounds, the following equation applies:
Process Variant (b):

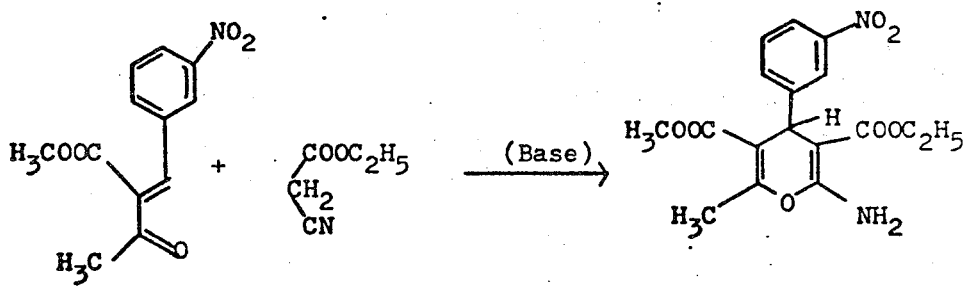

wherein $R^1$, $R^2$ and $R^3$ are as above defined except that $R^3$ is not —COOR'
in an inert organic solvent at a temperature of from about 10° C to about 200° C, to produce a compound wherein $R^3$ is other than —COOR', or
b. with a cyanoacetic acid ester of the formula

    IV wherein $R^3$ is —COOR' wherein R' is as above defined,
in an inert organic solvent at a temperature of from about 10° C to 200° C. to produce a compound wherein $R^3$ is —COOR'
wherein R' is as above defined,
and recovering the compound produced.

The two forms (a) and (b) of the process according to the invention are referred to throughout this specification as Process Variants (a) and (b).

According to one embodiment of the present invention
$R^1$ and $R^2$ are the same or different and each are alkyl of 1 to 4 carbon atoms;
$R^3$ is straight- or branched-chain alkyl of 1 to 4 carbon atoms, phenyl or —COOR' wherein R' is straight- or branched-chain alkyl of 1 to 5 carbon atoms, straight- or branched-chain alkenyl of 2 to 5 carbon atoms, straight- or branched-chain alkynyl of 2 to 5 carbon atoms, cycloalkyl of 3 to 5 carbon atoms, or cycloalkenyl of 3 to 5 carbon atoms;
$R^4$ is straight- or branched-chain alkyl of 1 to 6 carbon atoms, cycloalkyl of 3 to 6 carbon atoms, phenyl unsubstituted or substituted or substituted by 1 or 2 of the same or different substituents selected from the group consisting of alkyl of 1 to 4 carbon atoms, alkoxy of 1 to 4 carbon atoms, halogen (especially chloro or bromo), nitro, cyano, trifluoromethyl, carbalkoxy of 1 to 4 carbon atoms in the alkoxy moiety and $—SO_n$ alkyl wherein the alkyl moiety is of 1 to 4 carbon atoms and $n$ is 0 or 2, or naphthyl, pyridyl, thenyl or furyl unsubstituted or substituted by alkyl of 1 to 4 carbon atoms, alkoxy of 1 to 4 carbon atoms or halogen;

$R^5$ is straight- or branched-chain alkyl of 1 to 4 carbon atoms or $—OR''$ wherein $R''$ is straight- or branched-chain alkyl of 1 to 5 carbon atoms, straight- or branched-chain alkenyl of 2 to 5 carbon atoms, straight- or branched-chain alkynyl of 2 to 5 carbon atoms, cycloalkyl of 3 to 5 carbon atoms, cycloalkenyl of 3 to 5 carbon atoms, or straight- or branched-chain alkyl of 1 to 5 carbon atoms or alkenyl of 2 to 5 carbon atoms interrupted by 1 oxygen atom; and $R^6$ is hydrogen or alkyl of 1 to 4 carbon atoms.

According to another embodiment of the present invention $R^1$ and $R^2$ are the same or different and each are hydrogen, methyl or ethyl;

$R^3$ is methyl, ethyl, phenyl or $—COOR'$ wherein $R'$ is methyl, ethyl or allyl;

$R^4$ is methyl, phenyl unsubstituted or substituted by nitro, cyano, trifluoromethyl, chloro, methyl, carbethoxy, 1 to 3 methoxy moieties, nitro and methoxy, nitro and trifluoromethyl, nitro and thiomethyl, or nitro and chloro, or $R^4$ is naphthyl, pyridyl, quinolyl, furyl or thenyl;

$R^5$ is $—OR''$ wherein $R''$ is methyl, ethyl, propyl, allyl or cyclohexyl; and $R^6$ is methyl or ethyl.

According to another embodiment of the present invention $R^1$ and $R^2$ are the same or different and each are hydrogen, methyl or ethyl;

$R^3$ is methyl, carbomethoxy, or carbethoxy;

$R^4$ is methyl, phenyl, unsubstituted or substituted by nitro, chloro, trifluoromethyl, methyl, methoxy, cyano, carbethoxy or nitro and chloro; or $R^4$ is naphthyl, furyl or thenyl;

$R^5$ is methoxy, ethoxy, or propoxy; and $R^6$ is methyl.

The $\alpha,\beta$-unsaturated dicarbonyl compounds of general formula II are used as starting compounds in the process according to the invention are already known or can be manufactured according to known methods (Org. Reactions XV, 204 and thereafter (1967)).

Representative $\alpha,\beta$-unsaturated dicarbonyl compounds include:

Benzylideneacetoacetic acid methyl ester,
ethylideneacetoacetic acid methyl ester,
isopropylideneacetoacetic acid methyl ester,
2'-nitrobenzylideneacetoacetic acid methyl ester,
2'-nitrobenzylideneacetylacetone,
benzylideneacetylacetone,
3'-nitrobenzylideneacetoacetic acid methyl ester,
3'-nitrobenzylideneacetoacetic acid propargyl ester,
3'-nitrobenzylideneacetoacetic acid allyl ester,
3'-nitrobenzylideneacetoacetic acid $\beta$-methoxyethyl ester,
3'-nitrobenzylideneacetoacetic acid $\beta$-ethoxyethyl ester,
3'-nitrobenzylideneacetoacetic acid isopropyl ester,
3'-nitrobenzylideneacetylactone,
4'-nitrobenzylideneacetylactone,
4'-nitrobenzylideneacetoacetic acid $\beta$-propoxyethyl ester,
4'-nitrobenzylideneacetoacetic acid n-propyl ester,
3'-nitro-6'-chlorobenzylideneacetoacetic acid methyl ester,
2'-cyanobenzylideneacetoacetic acid methyl ester,
2'-cyanobenzylideneacetoacetic acid methyl ester,
2'-cyanobenzylideneacetoacetic acid ethyl ester,
2'-cyanobenzylidenepropionylactic acid ethyl ester,
3'-cyanobenzylideneacetoacetic acid methyl ester,
3'-nitro-4'-chlorobenzylideneacetylacetone,
3'-nitro-4'-chlorobenzylideneacetoacetic acid t-butyl ester,
3'-nitro-4'-chlorobenzylideneacetoacetic acid methyl ester,
2'-nitro-4'-methoxybenzylideneacetoacetic acid methyl ester,
2'-cyano-4'-methylbenzylideneacetoacetic acid ethyl ester,
2'-methylmercaptobenzylideneacetoacetic acid isopropyl ester,
2'-sulphonylmethylbenzylideneacetoacetic acid ethyl ester,
2'-sulphonylbenzylidenemethylacetoacetic acid allyl ester,
4-sulphonylmethylbenzylideneacetoacetic acid ethyl ester,
(1'-naphthylidene)-acetoacetic acid methyl ester,
(1'-naphthylidene)-acetoacetic acid ethyl ester,
(2'-naphthylidene)-acetoacetic acid ethyl ester,
(2'-ethoxy-1'-naphthylidene)-acetoacetic acid methyl ester,
(2'-methoxy-1'-naphthylidene)-acetoacetic acid ethyl ester,
5'-bromo-(1'-naphthylidene)-acetoacetic acid methyl ester,
(2'-quinolyl)-methylideneacetoacetic acid methyl ester,
(4'-quinolyl)-methylideneacetoacetic acid ethyl ester,
(8'-quinolyl)-methylideneacetoacetic acid ethyl ester,
$\alpha$-pyridylmethylideneacetoacetic acid methyl ester,
$\alpha$-pyridylmethylideneacetoacetic acid methyl ester,
$\alpha$-pyridylmethylideneacetoacetic acid ethyl ester,
$\alpha$-pyridylmethylideneacetoacetic acid allyl ester,
$\alpha$-pyridylmethylideneacetoacetic acid cyclohexyl ester,
$\beta$-pyridylmethylideneacetoacetic acid $\beta$-methoxyethyl ester,
$\gamma$-pyridylmethylideneacetoacetic acid methyl ester,
6-methyl-$\alpha$-pyridylmethylideneacetoacetic acid ethyl ester,
(2'-thenyl)-methylideneacetoacetic acid ethyl ester,
(2'-furyl)-methylideneacetoacetic acid allyl ester,
3'-nitrobenzylidenepropionylacetic acid ethyl ester,
$\alpha$-pyridylmethylidenepropionylacetic acid ethyl ester,
$\alpha$-pyridylmethylidenepropionylacetic acid methyl ester,
$\alpha$-pyridylmethylideneacetylactone-2'-, 3'- and 4'-methoxybenzylideneacetoacetic acid ethyl esters,
2'-, 3'- and 4'-methoxybenzylideneacetylacetone,
2'-methoxybenzylideneacetoacetic acid allyl ester,
2'-methoxybenzylidenacetoacetic acid allyl ester,
2'-methoxybenzylideneacetoacetic acid propargyl ester,
2'-methoxybenzylideneacetoacetic acid $\beta$-methoxyethyl ester, 2′-isopropoxybenzylideneacetoacetic acid ethyl ester,
3′-butoxybenzylideneacetoacetic acid methyl ester,
3′,4′,5′-trimethoxybenzylideneacetoacetic acid allyl estester,
2′-methylbenzylidenepropionylacetic acid methyl ester,
2′-,3′- and 4′-methylbenzylideneacetoacetic acid ethyl esters,
2′-methylbenzylideneacetoacetic acid β-methoxyethyl ester,
2′-methylbenzylideneacetoacetic acid β-propoxyethyl ester,
2′-methylbenzylideneacetoacetone,
3′,4′-dimethoxy-5′-bromobenzylideneacetoacetic acid ethyl ester,
2′-,3′- and 4′-chloro/bromo/fluorobenzylideneacetoacetic acid ethyl esters,
2′-fluorobenzylideneacetoacetic acid methyl ester,
3′-chlorobenzylideneacetylacetone,
3′-chlorobenzylidenepropionylacetic acid ethyl ester,
3′-chlorobenzylideneacetoacetic acid ethyl ester,
2′-chlorobenzylideneacetoacetic acid allyl ester,
2′-,3′- and 4′-trifluoromethylbenzylideneacetoacetic acid isopropyl ester,
3′-trifluoromethylbenzylideneacetoacetic acid methyl ester,
2′-carboethoxybenzylideneacetoacetic acid ethyl ester,
3′-carboxymethylbenzylideneacetoacetic acid methyl ester and
4′-carboxymethylbenzylideneacetoacetic acid allyl ester.

The inamines of formula III are used as starting compounds in Process Varient (a) according to the invention are already known or can be manufactured according to known methods (H. G. Viehe, M. Reinstein, Ang. Chem. 76, 537 (1964)).

Representative inamines include:
1-Dimethylamino-2-phenylacetylene,
1-diethylamino-2-phenylacetylene,
1-dimethylamino-3,3-dimethylbut-1-ine,
1-diethylaminoprop-1-ine,
1-diethylaminobut-1-ine and
1-diethylaminohex-1-ine.

The cyanoacetic acid esters of formula IV used as starting materials in Process Variant (b) according to the invention are already known (Inglis, Org. Synth. Coll., Vol. 1, 249 (1932)).

Representative cyanoacetic acid esters include:
cyanoacetic acid ethyl ester,
cyanoacetic acid methyl ester,
cyanoacetic acid propyl ester,
cyanoacetic acid isopropyl ester,
cyanoacetic acid butyl ester,
cyanoacetic acid allyl ester,
cyanoacetic acid propargyl ester and
cyanoacetic acid β-methoxyethyl ester.

Generally all inert organic solvents can be used as a solvent in the above process. Such solvents include, for example, alcohols (such as methanol, ethanol and propanol), ethers (such as diozane and diethyl ether) and hydrocarbons (such as cyclohexane, benzene, toluene and xylene). Preferably, according to Process Variant (a), toluene is used, and according to Process Variant (b), ethanol is used.

While the reaction temperatures can be varied over a substantial range (from about 10° to about 200° C) as indicated above, the preferred temperature range is between about 20° and about 180° C, and especially at about the boiling point of the solvent.

Process Variant (b) is preferably carried out in the presence of a basic condensation catalyst such as an organic base; for example, piperidine.

In carrying out the process of the present invention the starting materials are preferably reacted in substantially molar proportions.

Representative 2-amino-4 H-pyranes according to the present invention include:
a. 2-Amino-6-methyl-4-(2′-nitrophenyl)-4 H-pyrane-3,5-dicarboxylic acid diethyl ester.
b. 2-Amino-6-methyl-4-(2′-nitrophenyl)-4 H-pyrane-3,5-dicarboxylic acid 3-ethyl ester 5-methyl ester.
c. 2-Amino-6-ethyl-4-(3′-nitrophenyl)-4 H-pyrane-3,5-dicarboxylic acid diethyl ester.
d. 2-Amino-6-methyl-4-(3′-nitro-6′-methoxyphenyl)-4 H-pyrane-3,5-dicarboxylic acid diethyl ester.
e. 2-Amino-6-methyl-4-(2′-trifluoromethyl-4′-nitrophenyl)-4 H-pyrane-3,5-dicarboxylic acid 3-ethyl ester-5-methyl ester.
f. 2-Amino-6-methyl-4-(3′-nitro-6′-methylmercaptophenyl)-3,5-dicarboxylic acid dimethyl ester.
g. 2-Amino-6-methyl-4-(3′-cyanophenyl)-4 H-pyrane-3,5-dicarboxylic acid 3-allyl ester-5 ethyl ester.
h. 2-Amino-6-methyl-4-(3′-nitrophenyl)-4 H-pyrane-3,5-dicarboxylic acid 3-ethyl ester-5-cyclohexyl ester.
i. 2-Dimethylamino-3-methyl-6-ethyl-4-(3′-carbethoxyphenyl)-4 H-pyrane-5-carboxylic acid ethyl ester.
k. 2-Diethylamino-3-ethyl-6-methyl-4-(α-pyridyl)-4 H-pyrane-5-carboxylic acid isopropyl ester.
l. 2-Dimethylamino-3-methyl-6-ethyl-4-(2′-cyanophenyl)-4 H-pyrane-5-carboxylic acid ethyl ester.
m. 2-Diethylamino-3-phenyl-6-methyl-4-(2′-trifluoromethylphenyl)-4 H-pyrane-5-carboxylic acid ethyl ester.
n. 2-Diethylamino-3,6-dimethyl-4-(2′-naphthyl)-4 H-pyrane-5-carboxylic acid isopropyl ester.
o. 2-Diethylamino-3,6-dimethyl-4-(4′-quinolyl)-4 H-pyrane-5-carboxylic acid ethyl ester.
p. 2-Diethylamino-3-ethyl-6-methyl-4(3,4,5-trimethoxyphenyl)-4 H-pyrane-5-carboxylic acid allyl ester.

The compounds of the present invention have demonstrated the following pharmacological activity in animal tests:

1. On parenteral, oral and perlingual administration the compounds of the present invention produce a distinct and long-lasting dilation of the coronary vessels. This action on the coronary vessels is intensified by a simultaneous nitrile-like effect of reducing the load on the heart. The compounds influence or modify the heart metabolism in the sense of an energy saving.

2. The compounds of the present invention lower the blood pressure of normotonic and hypertonic animals and can thus be used as antipertensive agents.

3. The excitability of the stimulus formation and excitation conduction system within the heart is lowered so that an antifibrillation action demonstrable at therapeutic doses results.

4. The tone of the smooth muscle of the vessels is greatly reduced under the action of the compounds of the present invention. This vascular-spasmolytic action can take place in the entire vascular system or can manifest itself more or less isolated in circumscribed vascular regions (such as, for example, the central nervous system).

5. The compounds of the present invention have strongly muscular-spasmolytic actions which manifest themselves on the smooth muscle of the stomach, of the intestinal tract, of the urogenital tract and of the respiratory system.

6. The compounds of the present invention influence the cholesterol level and liquid level of the blood.

The compounds of the present invention may also be formulated into pharmaceutical compositions. The pharmaceutical compositions of the present invention contain a major or minor amount, e.g. from 99.5 to 0.1%, preferably 90 to 0.5%, of the active agent as herein defined in combination with a pharmaceutical carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application at one or more dosage units according to a predetermined dosage regimen, usually a whole, half, third, or quarter of the daily dosage administered once, twice, three or four times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the dosage for intravenal administration will be from 0.25 mg to 900 mg, preferably 1 to 450 mg. The preferred oral administration is 5 mg to 45 g, preferably 50 mg to 2.7 g. In each case, the dosage represents the amount of active ingredients to be administered. The daily dosage on i.v. administration is preferably 0.005 mg/kg to 10 mg/kg, particularly 0.02 to 5 mg/kg, and for oral administration is 0.1 to 50 mg/kg, particularly 1 to 30 mg/kg. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agaragar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like, can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with lowmelting, water-soluble or insoluble solids such as polyethylene glycol, cocoa butter, higher esters as, for example, myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons. Oral and intravenous compositions are preferred.

The coronary action of compounds representative of those of the present invention is set forth below in Table I:

Table I

| Compound of Preparative Example No. | Distinctly discernible rise in the oxygen saturation in the coronary sinus | |
|---|---|---|
| | Dose (mg/kg body weight intravenously) | Duration of Action |
| 1 | 0.5 | 90 mins |
| 4 | 0.5 | 30 mins |
| 6 | 5.0 | 20 mins |

The coronary action set out in Table I was ascertained on narcotized heart-catheterized mongrel dogs by measuring the rise in oxygen saturation in the coronary sinus.

The antihypertensive effect of compounds representative of those of the present invention as indicated by their blood-pressure-lowering effect is shown in Table II below. The dose quoted in the 3rd column is the dose required to lower the blood pressure of hypertensive rats by at least 15 mm Hg.

Table II

| Compound of Preparative Example No. | Toxicity in mice, mg/kg administered orally | Lowering of blood pressure in high blood pressure rats, mg/kg administered orally |
|---|---|---|
| 1 | | from 1.0 |
| 7 | | from 3.0 |
| 9 | | from 3.0 |

The following nonlimitative examples more particularly describe the present invention:

EXAMPLE 1

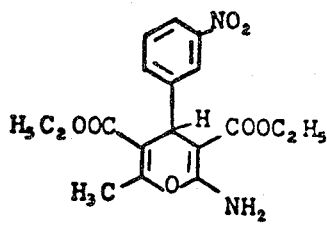

After heating a solution of 26.3 g of 3'-nitrobenzylideneacetoacetic acid ethyl ester, 11.3 g of cyanoacetic acid ethyl ester and 2 ml of piperidine in 100 ml of ethanol for 4 hours, 2-amino-6-methyl-4-(3'-nitrophenyl)-4H-pyrane-3,5-dicarboxylic acid diethyl ester of melting point 161°C (ethanol) was obtained. Yield 63% of theory.

EXAMPLE 2

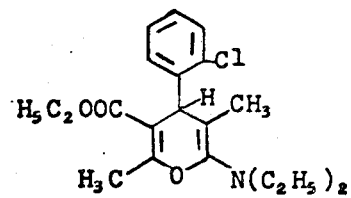

11.1 g of 1-diethylaminoprop-1-ine are added to a solution of 25.2 g of 2'-chlorobenzylideneacetoacetic acid ethyl ester in 100 ml of toluene. After the first exothermic reaction, the mixture is boiled for 4 hours under reflux and the residue is distilled: Boiling point at 0.9 mm. Hg: 205°C. 2-Diethylamino-3,6-dimethyl-4(2'-chlorophenyl)-4 H-pyrane-5-carboxylic acid ethyl ester. Yield 76% of theory.

EXAMPLE 3

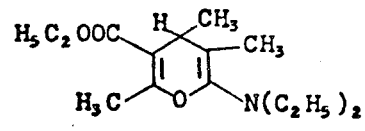

A solution of 15.6 g of ethylideneacetoacetic acid ethyl ester and 11.1 g of diethylaminoprop-1-ine is heated for 4 hours after the first vigorous reaction. The mixture is concentrated and the residue is distilled: Boiling point at 0.6 mm. Hg: 112°–126°C. 2-Diethylamino-3,4,6-trimethyl-4, H-pyrane-5-carboxylic acid ethyl ester. Yield 66% of theory.

EXAMPLE 4

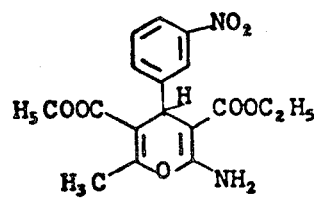

After boiling a solution of 24.9 g of 3'-nitrobenzylideneacetoacetic acid methyl ester, 11.3 g of cyanoacetic acid ethyl ester and 2 ml of piperidine in 100 ml of ethanol for 4 hours, 2-amino-6-methyl-4-(3'-nitrophenyl)-4 H-pyrane-3,5-dicarboxylic acid 3-ethyl ester-5-methyl ester of melting point 134°C was obtained. Yield 67% of theory.

EXAMPLE 5

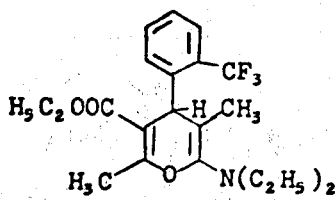

A solution of 28.6 g of 2'-trifluoromethylbenzylideneacetoacetic acid ethyl ester and 11.1 g of 1-diethylaminopro-p-1-ine in 200 ml of toluene is boiled for 4 hours under reflux after the first vigorous reaction. The mixture is concentrated and the residue is distilled: Boiling point at 0.1 mm. Hg: 139°–146°C. 2-Diethylamino-3,6-dimethyl-4-(2'-trifluoromethylphenyl)-4 H-pyrane-5-carboxylic acid ethyl ester. Yield 59% of theory.

EXAMPLE 6

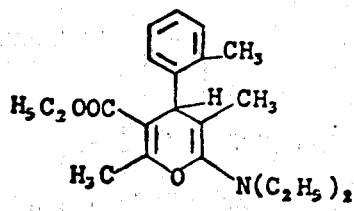

A solution of 23.2 g of 2'-methylbenzylideneacetoacetic acid ethyl ester and 11.1 g of 1-diethylaminoprop-1-ine in 150 ml of toluene is boiled for 4 hours under reflux after the first vigorous reaction. The mixture is concentrated and the residue distilled: Boiling point at 0.4 mm. Hg: 163°–174°C. 2-Diethylamino-3,6-dimethyl-4-(2'-methylphenyl)-4 H-pyrane-5-carboxylic acid ethyl ester.

EXAMPLE 7

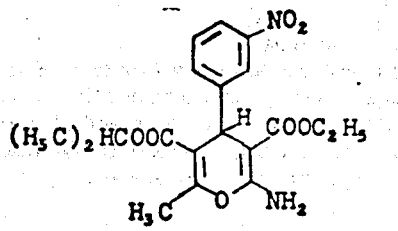

After heating a solution of 27.7 g of 3'-nitrobenzylideneacetoacetic acid isopropyl ester, 11.3 g of cyanoacetic acid ethyl ester and 2 ml of piperidine in 100 ml of ethanol for 4 hours, 2-amino-6-methyl-4-(3'-nitrophenyl)-4 H-pyrane-3,5-dicarboxylic acid 3-ethyl ester-5-isopropyl ester of melting point 135°C (ethanol) was obtained. Yield 46% of theory.

EXAMPLE 8

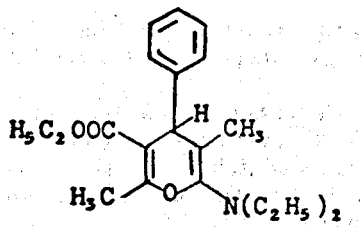

A solution of 21.8 g of benzylideneacetoacetic acid ethyl ester and 11.1 g of 1-diethylaminoprop-1-ine in 150 ml of toluene is boiled for 4 hours under reflux after the first vigorous reaction. The mixture is concentrated and the residue is distilled: Boiling point at 0.2 mm. Hg: 142°–155°C. 2-Diethylamino-3,6-dimethyl-4-phenyl-4 H-pyrane-5-carboxylic acid ethyl ester. Yield 62% of theory.

EXAMPLE 9

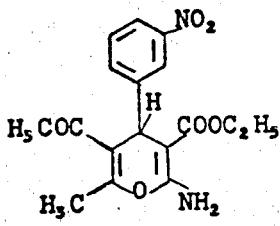

On heating a solution of 23.3 g of 3'-nitrobenzylideneacetylacetone, 11.3 g of cyanoacetic acid ethyl ester and 2 ml of piperidine in 100 ml of ethanol for 4 hours, 2-amino-5-acetyl-6-methyl-4-(3'-nitrophenyl)-4 H-pyrane-3-carboxylic acid ethyl ester of melting point 181°C (ethanol) was obtained. Yield 51% of theory.

EXAMPLE 10

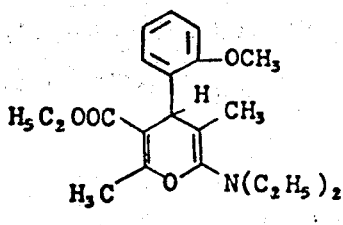

A solution of 24.8 g of 2'-methoxybenzylideneacetoacetic acid ethyl ester and 11.1 g of 1-diethylaminoprop-1-ine in 150 ml of toluene was boiled for 4 hours under reflux after the first vigorous reaction. The mixture is concentrated and the residue is distilled: Boiling point at 0.3 mm. Hg: 164°–168°C. 2-Diethylamino-3,6-dimethyl-4-(2'-methoxyphenyl)-4 H-pyrane-5-carboxylic acid ethyl ester. Yield 64% of theory.

EXAMPLE 11

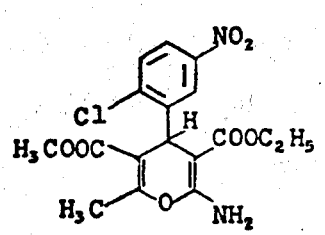

On heating a solution of 28.4 g of 3'-nitro-6'-chlorobenzylideneacetoacetic acid methyl ester, 11.4 g of cyanoacetic acid ethyl ester and 2 ml of piperidine in 100 ml of ethanol for 4 hours, 2-amino-6-methyl-4-(3'- nitro-6'-chlorophenyl)-4 H-pryane-3,5-dicarboxylic acid 3-ethyl ester-5-methyl ester of melting point 159°C was obtained. Yield 42% of theory.

EXAMPLE 12

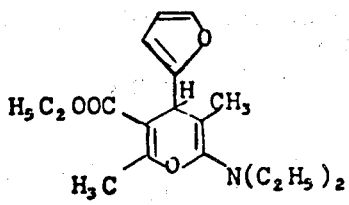

A solution of 21.0 g of 2'-furfurylideneacetoacetic acid ethyl ester and 11.1 g of 1-diethylaminoprop-1-ine in 150 ml of toluene was boiled for 4 hours under reflux after the first vigorous reaction. The mixture is concentrated and the residue is distilled: Boiling point at 0.8 mm. Hg: 159°–167°C. 2-Diethylamino-3,6-dimethyl-4-(2'-furyl)-4 H-pryane-5-carboxylic acid ethyl ester.

EXAMPLE 13

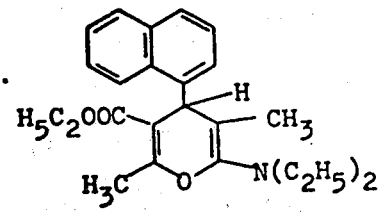

11.1 g of 1-diethylaminoprop-1-ine are added to a solution of 26.8 g of (1'-naphthylidene)-acetoacetic acid ethyl ester in 100 ml of toluene. After the first exothermic reaction, the mixture is boiled for 4 hours under reflux and the residue is distilled: Boiling point at 215 mm. Hg: 210°–222°C. 2-Diethylamino-3,6-dimethyl-4-(1'-naphthyl)-4 H-pyrane-5-carboxylic acid ethyl ester. Yield: 38% of theory.

EXAMPLE 14

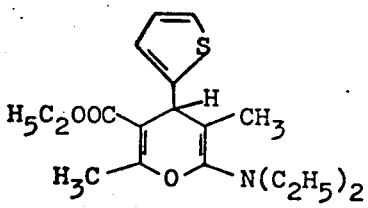

11.1 g of 1-diethylaminoprop-1-ine are added to a solution of 22.4 g of (2'-thenylidene)-acetoacetic acid ethyl ester in 100 ml of toluene. After the first exothermic reaction, the mixture is boiled for 4 hours under reflux and the residue is distilled: Boiling point at 2 mm. Hg: 184°–189°C. 2-Diethylamino-3,6-dimethyl-4-(2'-thenyl)-4 H-pyrane-5-carboxylic acid ethyl ester. Yield: 59% of theory.

EXAMPLE 15

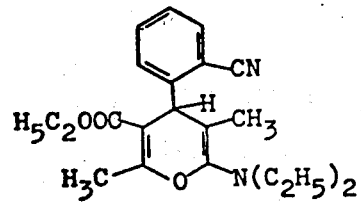

11.1 g of 1-diethylaminoprop-1-ine are added to a solution of 24.3 g of 2'-cyanobenzylideneacetoacetic acid ethyl ester in 100 ml of toluene. After the first exothermic reaction, the mixture is boiled for 4 hours under reflux and the residue is distilled: Boiling point at 2 mm. Hg: 188°–192°C. 2-Diethylamino-3,6-dimethyl-4-(2'-cyanophenyl)-4 H-pyrane-5-carboxylic acid ethyl ester. Yield 46% of theory.

EXAMPLE 16

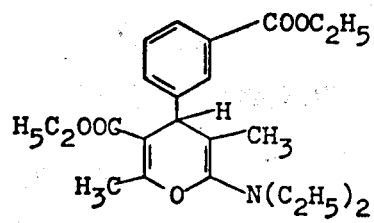

11.1 g of 1-diethylaminoprop-1-ine are added to a solution of 29.0 g of 3'-ethoxycarbonylbenzylideneacetoacetic acid ethyl ester in 100 ml of toluene. After the first exothermic reaction, the mixture is boiled for 4 hours under reflux and the residue is distilled: Boiling point at 1.3mm Hg: 213°–217°C. 2-Diethylamino-3,6-dimethyl-4-(3'-ethoxycarbonyl-phenyl)-4 H-pyrane-5-carboxylic acid ethyl ester. Yield: 41% of theory.

What is claimed is:

1. A pharmaceutical composition useful for effecting vasodilating action in humans and animals and for treating hypertension in humans and animals which comprises a vasodilating amount or an antihypertensive amount of a compound of the formula

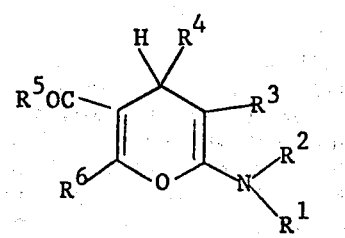

wherein $R^1$ and $R^2$ are the same or different and are each hydrogen or straight- or branched-chain lower alkyl;

$R^3$ is straight- or branched-chain lower alkyl, phenyl or —COOR' wherein R' is straight, branched or cyclic lower alkyl, lower alkenyl or lower alkynyl;

$R^4$ is phenyl unsubstituted or substituted by 1, 2 or 3 of the same or different substituents selected from the group consisting of lower alkyl, lower alkoxy, halogen, nitro, cyano, trifluoromethyl, carb(lower alkoxy) and —SO$_n$ lower alkyl wherein $n$ is 0, 1 or 2, or naphthyl;

R$^5$ is straight, branched or cyclic lower alkyl or —OR″ wherein R″ is straight, branched or cyclic lower alkyl, lower alkenyl or lower alkynyl or straight, branched or cyclic lower alkyl, lower alkenyl or lower alkynyl substituted by 1 or 2 oxygen atoms; and R$^6$ is hydrogen or lower alkyl, in combination with a pharmaceutically acceptable nontoxic inert diluent or carrier.

2. A composition according to claim 1 wherein
R$^1$ and R$^2$ are the same or different and each are alkyl of 1 to 4 carbon atoms;

R$^3$ is straight- or branched-chain alkyl of 1 to 4 carbon atoms, phenyl or —COOR′ wherein R′ is straight- or branched-chain alkyl of 1 to 5 carbon atoms, straight- or branched-chain alkenyl of 2 to 5 carbon atoms, straight- or branched-chain alkynyl of 2 to 5 carbon atoms, cycloalkyl of 3 to 5 carbon atoms, or cycloalkenyl of 3 to 5 carbon atoms;

R$^4$ is phenyl unsubstituted or substituted or substituted by 1 or 2 of the same or different substituents selected from the group consisting of alkyl of 1 to 4 carbon atoms, alkoxy of 1 to 4 carbon atoms, halogen, nitro, cyano, trifluoromethyl, carbalkoxy of 1 to 4 carbon atoms in the alkoxy moiety and —SO$_n$ alkyl wherein the alkyl moiety is of 1 to 4 carbon atoms and $n$ is 0 or 2, or naphthyl;

R$^5$ is straight- or branched-chain alkyl of 1 to 4 carbon atoms or —OR″ wherein R″ is straight- or branched-chain alkyl of 1 to 4 carbon atoms, straight- or branched-chain alkenyl of 2 to 5 carbon atoms, straight- or branched-chain alkynyl of 2 to 5 carbon atoms, cycloalkyl of 3 to 5 carbon atoms, cycloalkenyl of 3 to 5 carbon atoms, or straight- or branched-chain alkyl of 1 to 5 carbon atoms or alkenyl of 2 to 5 carbon atoms interrupted by 1 oxygen atom; and R$^6$ is hydrogen or alkyl of 1 to 4 carbon atoms.

3. A composition according to claim 1 wherein
R$^1$ and R$^2$ are the same or different and each are hydrogen, methyl or ethyl;

R$^3$ is methyl, ethyl, phenyl or —COOR′ wherein R′ is methyl, ethyl or allyl;

R$^4$ is phenyl unsubstituted or substituted by nitro, cyano, trifluoromethyl, chloro, methyl, carbethoxy, 1 to 3 methoxy moieties, nitro and methoxy, nitro and trifluoromethyl, nitro and thiomethyl, or nitro and chloro, or R$^4$ is naphthyl;

R$^5$ is —OR″ wherein R″ is methyl, ethyl, propyl, allyl or cyclohexyl; and

R$^6$ is methyl or ethyl.

4. A composition according to claim 1 wherein
R$^1$ and R$^2$ are the same or different and each are hydrogen, methyl or ethyl;

R$^3$ is methyl, carbomethoxy, or carbethoxy;

R$^4$ is phenyl, unsubstituted or substituted by nitro, chloro, trifluoromethyl, methyl, methoxy, cyano, carbethoxy or nitro and chloro; or R$^4$ is naphthyl;

R$^5$ is methoxy, ethoxy, or propoxy; and

R$^6$ is methyl.

5. The composition according to claim 1 wherein the compound is 2-amino-6-methyl-4-(2′-nitrophenyl)-4 H-pyrane-3,5-dicarboxylic acid diethyl ester.

6. The composition according to claim 1 wherein the compound is 2-amino-6-methyl-4-(2′-nitrophenyl)-4 H-pyrane-3,5-dicarboxylic acid 3-ethyl ester 5-methyl ester.

7. The composition according to claim 1 wherein the compound is 2-amino-6-ethyl-4-(3′-nitrophenyl)-4 H-pyrane-3,5-dicarboxylic acid diethyl ester.

8. The composition according to claim 1 wherein the compound is 2-amino-6-methyl-4-(3′-nitro-6′-methoxyphenyl)-4 H-pyrane-3,5-dicarboxylic acid diethyl ester.

9. The composition according to claim 1 wherein the compound is 2-amino-6-methyl-4-(2′-trifluoromethyl-4′-nitrophenyl)-4 H-pyrane-3,5-dicarboxylic acid 3-ethyl ester-5-methyl ester.

10. The composition according to claim 1 wherein the compound is 2-amino-6-methyl-4-(3′-nitro-6′-methylmercaptophenyl)-3,5-dicarboxylic acid dimethyl ester.

11. The composition according to claim 1 wherein the compound is 2-amino-6-methyl-4-(3′-cyanophenyl)-4 H-pyrane-3,5-dicarboxylic acid 3-allyl ester-5 ethyl ester.

12. The composition according to claim 1 wherein the compound is 2-amino-6-methyl-4-(3′-nitrophenyl)-4 H-pyrane-3,5-dicarboxylic acid 3-ethyl ester-5-cyclohexyl ester.

13. The composition according to claim 1 wherein the compound is 2-dimethylamino-3-methyl-6-ethyl-4-(3′-carbethoxyphenyl)-4 H-pyrane-5-carboxylic acid ethyl ester.

14. The composition according to claim 1 wherein the compound is 2-dimethylamino-3-methyl-6-ethyl-4-(2′-cyanophenyl)-4 H-pyrane-5-carboxylic acid ethyl ester.

15. The composition according to claim 1 wherein the compound is 2-diethylamino-3-phenyl-6-methyl-4-(2′-trifluoromethylphenyl)-4 H-pyrane-5-carboxylic acid ethyl ester.

16. The composition according to claim 1 wherein the compound is 2-diethylamino-3,6-dimethyl-4-(2′-naphthyl)-4 H-pyrane-5-carboxylic acid isopropyl ester.

17. The composition according to claim 1 wherein the compound is 2-diethylamino-3-ethyl-6-methyl-4-(3,4,5-trimethoxyphenyl)-4 H-pyrane-5-carboxylic acid allyl ester.

18. The composition according to claim 1 wherein the compound is

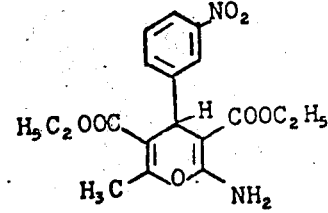

19. The composition according to claim 1 wherein the compound is

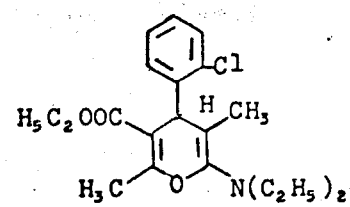

20. The composition according to claim 1 wherein the compound is

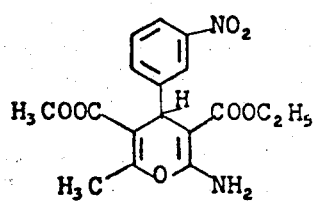

21. The composition according to claim 1 wherein the compound is

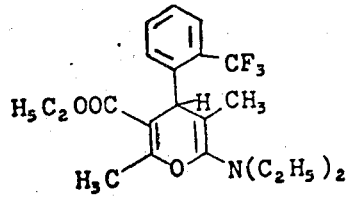

22. The composition according to claim 1 wherein the compound is

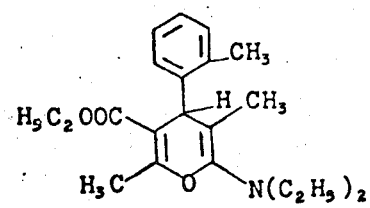

23. The composition according to claim 1 wherein the compound is

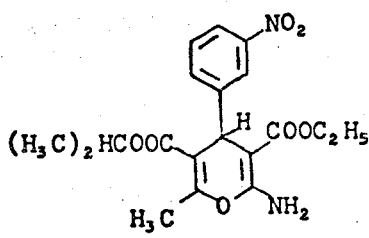

24. The composition according to claim 1 wherein the compound is

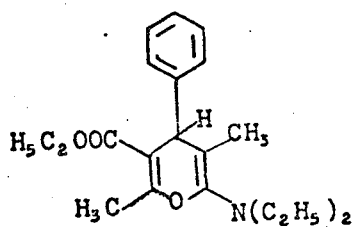

25. The composition according to claim 1 wherein the compound is

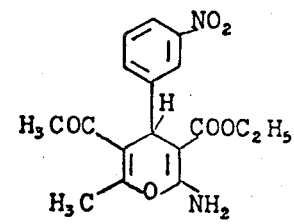

26. The composition according to claim 1 wherein the compound is

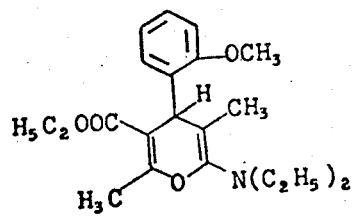

27. The composition according to claim 1 wherein the compound is

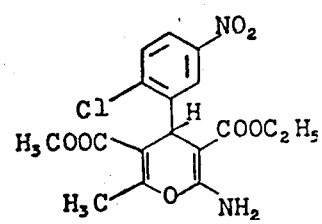

28. The composition according to claim 1 wherein the compound is

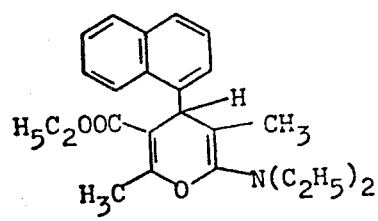

29. The composition according to claim 1 wherein the compound is

30. The composition according to claim 1 wherein the compound is

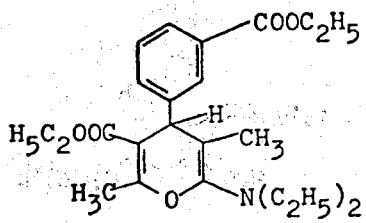

31. A composition according to claim 1 in oral administration form.

32. A composition according to claim 1 in parenteral administration form.

33. A method of producing vasodilating action in humans and animals and a method of treating hypertension in humans and animals which comprises administering to such human or animal a vasodilating amount or an anti-hypertensive amount of a compound of the formula:

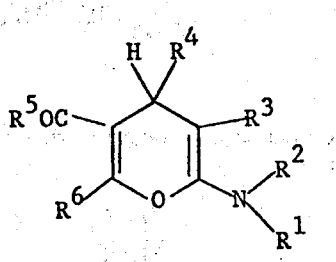

wherein
$R^1$ and $R^2$ are the same or different and are each hydrogen or straight- or branched-chain lower alkyl;
$R^3$ is straight- or branched-chain lower alkyl, phenyl or —COOR' wherein R' is straight, branched or cyclic lower alkyl, lower alkenyl or lower alkynyl;
$R^4$ is phenyl unsubstituted or substituted by 1, 2 or 3 of the same or different substituents selected from the group consisting of lower alkyl, lower alkoxy, halogen, nitro, cyano, trifluoromethyl, carb(lower alkoxy) and —SO$_n$ lower alkyl wherein $n$ is 0, 1 or 2, or naphthyl;
$R^5$ is straight, branched or cyclic lower alkyl or —OR'' wherein R'' is straight, branched or cyclic lower alkyl, lower alkenyl or lower alkynyl or straight, branched or cyclic lower alkyl, lower alkenyl or lower alkynyl substituted by 1 or 2 oxygen atoms; and
$R^6$ is hydrogen or lower alkyl.

34. A method according to claim 33 wherein
$R^1$ and $R^2$ are the same or different and each are alkyl or 1 to 4 carbon atoms;
$R^3$ is straight- or branched-chain alkyl of 1 to 4 carbon atoms, phenyl or —COOR' wherein R' is straight- or branched-chain alkyl of 1 to 5 carbon atoms, straight- or branched-chain alkenyl of 2 to 5 carbon atoms, straight- or branched-chain alkynyl of 2 to 5 carbon atoms, cycloalkyl of 3 to 5 carbon atoms, or cycloalkenyl of 3 to 5 carbon atoms;
$R^4$ is phenyl unsubstituted or substituted or substituted by 1 or 2 of the same or different substituents selected from the group consisting of alkyl of 1 to 4 carbon atoms, alkoxy of 1 to 4 carbon atoms, halogen, nitro, cyano, trifluoromethyl, carbalkoxy of 1 to 4 carbon atoms in the alkoxy moiety and —SO$_n$ alkyl wherein the alkyl moiety is of 1 to 4 carbon atoms and $n$ is 0 or 2, or naphthyl;
$R^5$ is straight- or branched-chain alkyl of 1 to 4 carbon atoms or —OR'' where R'' is straight- or branched-chain alkyl of 1 to 4 carbon atoms, straight- or branched-chain alkenyl of 2 to 5 carbon atoms, straight- or branched-chain alkynyl of 2 to 5 carbon atoms, cycloalkyl of 3 to 5 carbon atoms, cycloalkenyl of 3 to 5 carbon atoms, or straight- or branched-chain alkyl of 1 to 5 carbon atoms or alkenyl of 2 to 5 carbon atoms interrupted by 1 oxygen atom; and
$R^6$ is hydrogen or alkyl of 1 to 4 carbon atoms.

35. A method according to claim 33 wherein
$R^1$ and $R^2$ are the same or different and each are hydrogen, methyl or ethyl;
$R^3$ is methyl, ethyl, phenyl or —COOR' wherein R' is methyl, ethyl or allyl;
$R^4$ is phenyl unsubstituted or substituted by nitro, cyano, trifluoromethyl, chloro, methyl, carbethoxy, 1 to 3 methoxy moieties, nitro and methoxy, nitro and trifluoromethyl, nitro and thiomethyl, or nitro and chloro, or
$R^4$ is naphthyl;
$R^5$ is —OR'' wherein R'' is methyl, ethyl, propyl, allyl or cyclohexyl; and
$R^6$ is methyl or ethyl.

36. A method according to claim 33 wherein
$R^1$ and $R^2$ are the same or different and each are hydrogen, methyl or ethyl;
$R^3$ is methyl, carbomethoxy, or carbethoxy;
$R^4$ is phenyl, unsubstituted or substituted by nitro, chloro, trifluoromethyl, methyl, methoxy, cyano, carbethoxy or nitro and chloro; or
$R^4$ is naphthyl;
$R^5$ is methoxy, ethoxy, or propoxy; and
$R^6$ is methyl.

37. The method according to claim 33 wherein the compound is 2-amino-6-methyl-4-(2'-nitrophenyl)-4 H-pyrane-3,5-dicarboxylic acid diethyl ester.

38. The method according to claim 33 wherein the compound is 2-amino-6-methyl-4-(2'-nitrophenyl)-4 H-pyrane-3,5-dicarboxylic acid 3-ethyl ester 5-methyl ester.

39. The method according to claim 33 wherein the compound is 2-amino-6-ethyl-4-(3'-nitrophenyl)-4 H-pyrane-3,5-dicarboxylic acid diethyl ester.

40. The method according to claim 33 wherein the compound is 2-amino-6-methyl-4-(3'-nitro-6'-methoxyphenyl)-4 H-pyrane-3,5-dicarboxylic acid diethyl ester.

41. The method according to claim 33 wherein the compound is 2-amino-6-methyl-4-(2'-trifluoromethyl-4'-nitrophenyl)-4 H-pyrane-3,4-dicarboxylic acid 3-ethyl ester-5-methyl ester.

42. The method according to claim 33 wherein the compound is 2-amino-6-methyl-4-(3'-nitro-6'-methylmercaptophenyl)-3,5-dicarboxylic acid dimethyl ester.

43. The method according to claim 33 wherein the compound is 2-amino-6-methyl-4-(3'-cyanophenyl)-4 H-pyrane-3,5-dicarboxylic acid 3-allyl ester-5-ethyl ester.

44. The method according to claim 33 wherein the compound is 2-amino-6-methyl-4-(3'-nitrophenyl)-4 H-pyrane-3,5-dicarboxylic acid 3-ethyl ester-5-cyclohexyl ester.

45. The method according to claim 33 wherein the compound is 2-dimethylamino-3-methyl-6-ethyl-4-(3'-carbethoxyphenyl)-4 H-pyrane-5-carboxylic acid ethyl ester.

46. The method according to claim 33 wherein the compound is 2-dimethylamino-3-methyl-6-ethyl-4-(2'-cyanophenyl)-4 H-pyrane-5-carboxylic acid ethyl ester.

47. The method according to claim 33 wherein the compound is 2-diethylamino-3-phenyl-6-methyl-4-(2'-trifluoromethylphenyl)-4 H-pyrane-5-carboxylic acid ethyl ester.

48. The method according to claim 33 wherein the compound is 2-diethylamino-3,6-dimethyl-4-(2'-naphthyl)-4 H-pyrane-5-carboxylic acid isopropyl ester.

49. The method according to claim 33 wherein the compound is 2-diethylamino-3-ethyl-6-methyl-4-(3,4,5-trimethoxyphenyl)-4 H-pyrane-5-carboxylic acid allyl ester.

50. The method according to claim 33 wherein the compound is

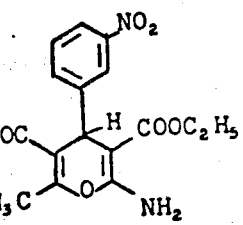

51. The method according to claim 33 wherein the compound is

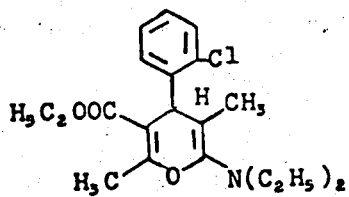

52. The method according to claim 33 wherein the compound is

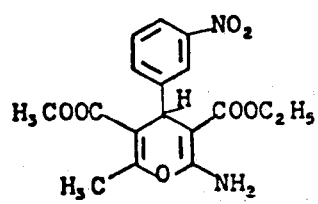

53. The method according to claim 33 wherein the compound is

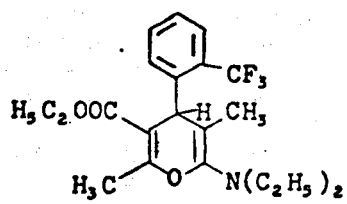

54. The method according to claim 33 wherein the compound is

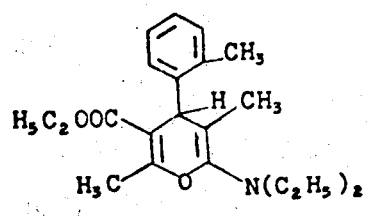

55. The method according to claim 33 wherein the compound is

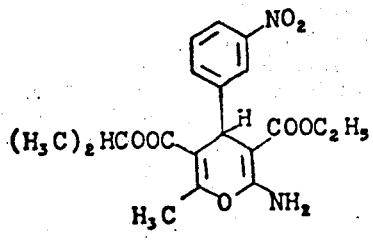

56. The method according to claim 33 wherein the compound is

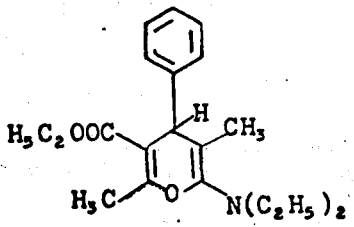

57. The method according to claim 33 wherein the compound is

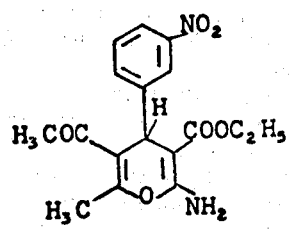

58. The method acording to claim 33 wherein the compound is

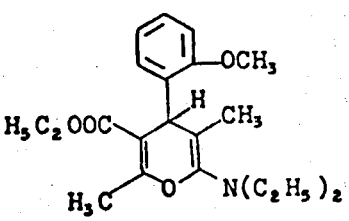

59. The method according to claim 33 wherein the compound is
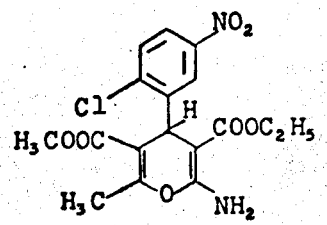
60. The method according to claim 33 wherein the compound is
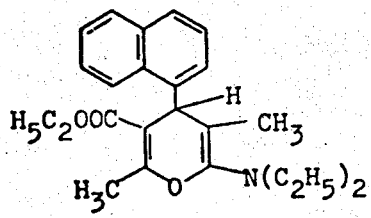
61. The method according to claim 33 wherein the compound is
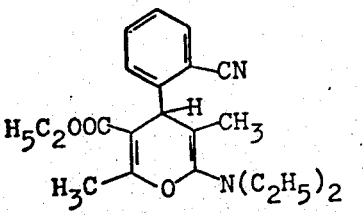
62. The method according to claim 33 wherein the compound is
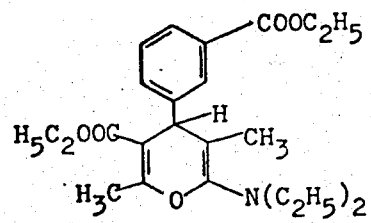
63. A method according to claim 33 wherein the administration is oral.
64. A method according to claim 33 wherein the administration is parenteral.
* * * * *